(12) United States Patent
Shaw et al.

(10) Patent No.: US 7,759,539 B2
(45) Date of Patent: Jul. 20, 2010

(54) WOUND DRESSING

(75) Inventors: Helen Shaw, Widnes (GB); Patrick G. Linnane, Chester (GB)

(73) Assignee: ConvaTec Technologies Inc., Las Vegas, NV (US)

( * ) Notice: Subject to any disclaimer, the term of this patent is extended or adjusted under 35 U.S.C. 154(b) by 1605 days.

(21) Appl. No.: 10/755,107

(22) Filed: Jan. 9, 2004

(65) Prior Publication Data
US 2004/0181182 A1 Sep. 16, 2004

(30) Foreign Application Priority Data
Jan. 10, 2003 (GB) ................................. 0300625.1

(51) Int. Cl.
*A61F 13/00* (2006.01)
*A61L 15/00* (2006.01)

(52) U.S. Cl. ..................... 602/52; 424/445; 604/304

(58) Field of Classification Search .................. 602/42, 602/43, 46, 48, 52, 54, 56, 41, 55; 424/443–448; 604/304–308
See application file for complete search history.

(56) References Cited

U.S. PATENT DOCUMENTS

| | | | | |
|---|---|---|---|---|
| 4,906,240 A | * | 3/1990 | Reed et al. ................. | 604/307 |
| 4,909,244 A | * | 3/1990 | Quarfoot et al. ............. | 602/48 |
| 5,135,755 A | | 8/1992 | Czech et al. | |
| 5,183,664 A | * | 2/1993 | Ansell ....................... | 424/445 |
| 5,204,110 A | * | 4/1993 | Cartmell et al. ............. | 424/443 |
| 6,075,177 A | * | 6/2000 | Bahia et al. .................. | 602/43 |
| 6,153,214 A | | 11/2000 | Horsler | |
| 6,201,164 B1 | | 3/2001 | Wulff et al. | |
| 6,548,730 B1 | * | 4/2003 | Patel et al. ................... | 602/56 |
| 7,041,868 B2 | * | 5/2006 | Greene et al. ................ | 602/48 |
| 2002/0038099 A1 | * | 3/2002 | Griffiths et al. .............. | 602/54 |
| 2003/0153860 A1 | * | 8/2003 | Nielsen et al. ................ | 602/43 |

FOREIGN PATENT DOCUMENTS

| | | |
|---|---|---|
| EP | 0426422 A3 | 5/1991 |
| EP | 0509703 A1 | 10/1992 |
| WO | WO 94/16746 | 8/1994 |
| WO | WO 99/12581 | 3/1999 |
| WO | WO 00/01425 | 1/2000 |
| WO | WO 01/91681 A1 | 12/2001 |

* cited by examiner

*Primary Examiner*—Patricia M Bianco
*Assistant Examiner*—Tarla R Patel
(74) *Attorney, Agent, or Firm*—John M. Kilcoyne

(57) ABSTRACT

A wound dressing for post-operative sites comprising: a thin film layer covered on one side with an adhesive and an absorbent layer adhered to the adhesive side of the thin film layer, the absorbent layer being capable of absorbing exudate to allow the wound to be viewed through the dressing.

14 Claims, 1 Drawing Sheet

WOUND DRESSING

The present invention relates to a wound dressing particularly, but not exclusively, for use as a dressing on post-operative wounds.

BACKGROUND OF THE INVENTION

It is known to make thin film wound dressings for use on post-operative wound sites comprising a thin polymeric film with an adhesive coating. Such a dressing is sold under the name OpSite™ by Smith and Nephew. Thin film dressings when used alone, are generally used on closed wounds with little or no exudate. These thin film dressings have achieved popularity in part because the dressings are capable of readily conforming to the shape of the body thus rendering them more comfortable to wear For wounds producing some exudate, post-operative wound dressings may be of the type which comprise a thin polymeric film and a low adherency absorbent pad. Such a dressing is sold under the name OpSite Post-Op™ by Smith and Nephew. A disadvantage of such dressings is that the absorbent pad, although generally non-adherent, is not transparent meaning that the wound cannot be seen through the dressing. This is important as seeing the wound allows the nursing and surgical staff to check healing progression and assess whether the wound has become infected, or whether the dressing needs changing. In the past, with such dressings, it has only been possible to see the wound by removing the dressing. This risks skin damage and disturbance of the healing process. The absorbent pad also reduces greatly the flexibility of the dressing meaning that a post-operative dressing with an absorbent pad may be difficult to apply to certain areas of the body and may be uncomfortable to wear.

There is thus a need for a wound dressing suitable for use on post-operative wounds which is capable of absorbing exudate at the rate generally produced by such wounds but which allows the wound to be viewed with the dressing in place.

SUMMARY OF THE INVENTION

We have now invented a wound dressing for post-operative sites which alleviates the above problems by combining absorption and the capability to view the wound through the dressing, the dressing being in a conformable format and there is provided by a first embodiment of the present invention a wound dressing for post-operative sites comprising:
(1) a thin film layer covered on one side with an adhesive and
(2) an absorbent layer adhered to the adhesive side of the thin film layer, the absorbent layer being capable of absorbing exudate to allow the wound to be viewed through the dressing.

DETAILED DESCRIPTION OF THE INVENTION

Figure 1:
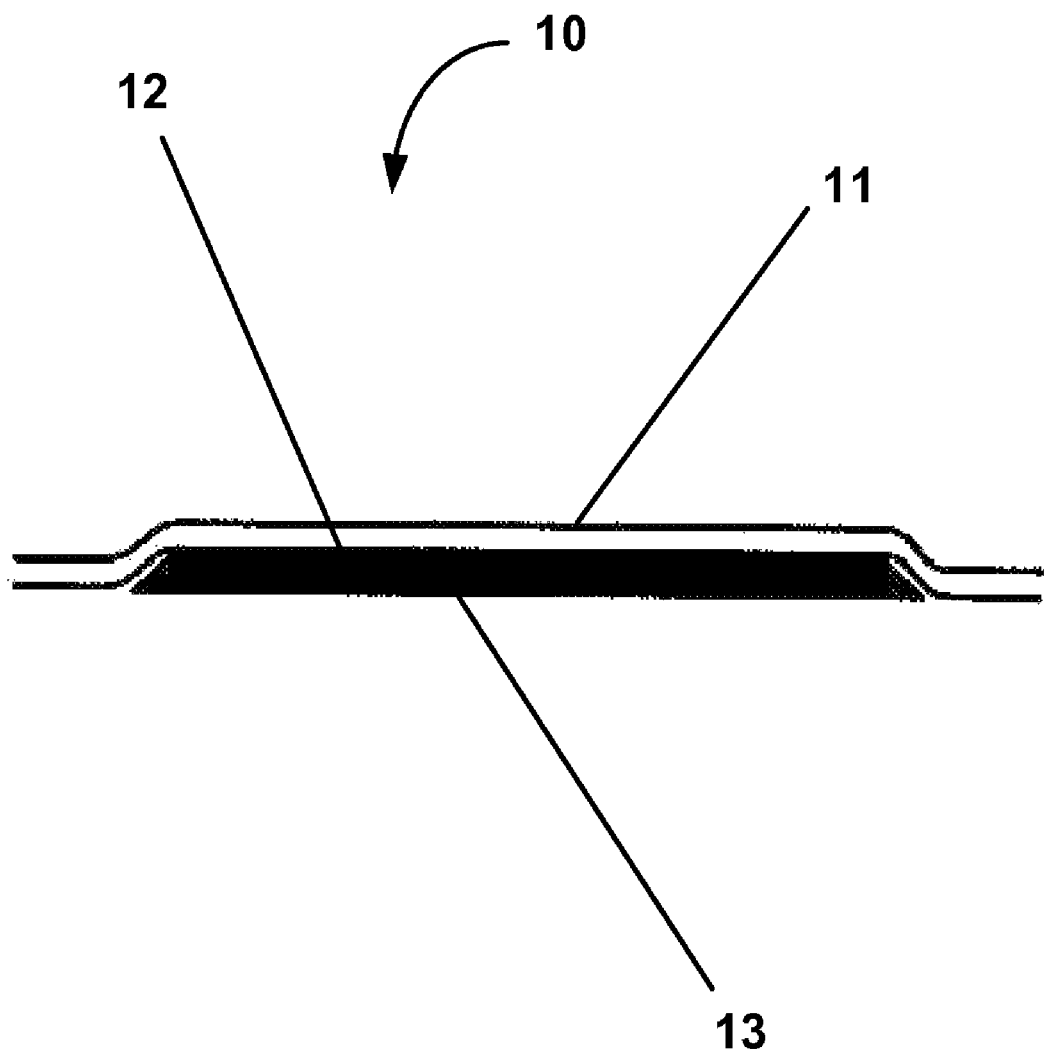
FIG. 1 is a cross-sectional view of the wound dressing.

We have found that wound dressings according to the invention may mitigate the problems associated with the viewing of wounds yet be readily conformable to highly contoured wound sites. It is thought that this is in part achieved by the selection of the absorbent layer which provides absorbency without adding to the bulk of the dressing and which allows the wound to be viewed on the absorption of exudate and preferably before the absorption of exudate. This allows the wound to be viewed without removal of the dressing.

As shown in FIG. 1, the thin film layer 11 provides a viral and bacterial barrier to the wound. It is preferably made from polyurethane, has a thickness of 0.02 mm to 0.04 mm and is transparent. Preferably the thin film layer has a high MVTR. This allows moisture to evaporate from the dressing. The film layer 11 preferably has an MVTR of at least 2500 gsm/24 hrsas measured by the method described in BP 1993 Appendix XX J1 or in the range of from 1000 gsm/24 hrs to 10000 gsm/24 hrs, preferably 2500 gsm/24 hrs to 5000 gsm/24 hrs.

The absorbent layer 13 is present to absorb exudate from the wound. The absorbent layer 13 preferably has an absorbency of at least 10 g of sodium chloride and calcium chloride solution (BP 1995 Appendix 1A) per gram of absorbent layer as measured by the absorbency test for alginate dressings BP 1995. The absorbent layer 13 preferably forms the wound contact layer of the dressing 10 and forms a transparent gel on contact with exudate which gel comes into intimate contact with the wound and helps to increase conformability and mobility at the wound site. The absorbent layer 13 is preferably fibrous and most preferably comprises gel forming fibres.

The gel forming fibres are preferably chemically modified cellulosic fibres in the form of a fabric and in particular carboxymethylated cellulose fabrics as described in WO/00/01425 to Akzo Nobel UK Ltd. The carboxymethylated cellulosic fabrics preferably have a degree of substitution of between 0.12 to 0.35 as measured by IR spectroscopy (as defined in WO/00/01425) more preferably a degree of substitution of between 0.20 and 0.30 and are made by carboxymethylating a woven or non-woven cellulosic fabric such that the absorbency is increased. Particularly preferred fabrics have an absorbency of between 15 g/g of sodium/calcium chloride as defined above to 30 g/g of sodium/calcium chloride as measured by the method defined above. Particularly preferred fabrics have an absorbency of 20 g/g to 30 g/g and most preferred of 25 g/g to 28 g/g of sodium/calcium chloride as measured by the method defined above.

The cellulosic fabric preferably consists solely of cellulosic fibre but may contain a proportion of non-cellulosic textile fibre or of gel-forming fibre. The cellulosic fibre is of known kind and may comprise continuous filament yarn and/or staple fibre. The carboxymethylation is generally performed by contacting the fabric with strong alkali and a carboxymethylating agent such as chloracetic acid in an aqueous system.

The fabric is preferably of a non-woven type to reduce fibre shedding in the wound on cutting of the dressing and more preferably has a surface structure that provides a key for adhesion of the thin film layer. Such a surface structure could be provided by a fabric which is hydroentangled and thus comprises a series of apertures on a microscopic scale.

The absorbent layer 13 preferably has a low lateral wicking rate so that exudate is not spread across the full extent of the layer. This has the advantage of reducing maceration in the skin surrounding the wound. Preferably the lateral wicking rate is from 10 mm per minute to 40 mm per minute. More preferably the lateral wicking rate is from 10 to 20 mm per minute.

The adhesive layer 12 of the present invention is applied to the thin film layer 11 and may adhere the dressing to the skin for instance where the absorbent layer 13 is an island surrounded by the thin film 11. Preferably the adhesive composition comprises a homogeneous blend of one or more water soluble hydrocolloids and one or more low molecular weight polyisobutylenes such as are described in EP-B-92999 incorporated herein by reference. The water soluble hydrocolloids may be selected from sodium carboxymethylcellulose, pectin, gelatin, guar gum, locust bean gum, gum karaya and mixtures thereof. The polyisobutylenes may be selected from low molecular weight polyisobutylenes having a viscosity average molecular weight of from 36,000 to 58,000 Florey. The adhesive layer 12 is capable of absorbing exudate while maintaining adhesion of the dressing to the skin.

Alternatively the adhesive composition may comprise a homogeneous blend of one or more hyrdocolloids, one or more low molecular weight polyisobutylenes one or more styrene block copolymers, mineral oil, butyl rubber, a tackifier and small amounts of optional components. By selection of specific ranges of the amounts of the above listed components, adhesive compositions may be prepared having good adhesion to the skin and stretchability. Such compositions and the preparation thereof are disclosed in EP-B-130061 incorporated herein by reference.

The dressing 10 will typically be made in three sizes, all dressings preferably being about 0.6 mm thick.

Preferred embodiments of the invention will now be illustrated in the following examples.

Example 1

A wound dressing 10 according to the invention was made by obtaining an absorbent layer 13 as described in WO 00/01425 and generally in Example 2 of that patent application having an absorbency of 25 g/g and a lateral wicking rate of 11 mm per minute in the form of a hydroentangled apertured fabric and bonding it to a polyurethane film coated with a hydrocolloid adhesive described above by conventional heat lamination/pressure techniques. Dressings were press cut or roller cut from the laminated web.

Example 2

The in use characteristics of various embodiments of the present invention are compared to a commercially available post operative dressing. On application to the wound, the dressing of Example 1 is semi transparent but on absorption of exudate becomes transparent allowing the wound to be viewed. On application to the wound the commercially available post operative dressing is opaque and on absorption of exudate, remains opaque.

Example 3

To demonstrate the difference in transparency between the dressing of Example 1 and typical prior art dressings a Kodak grey scale card was used to provide a numerical indication of visibility through the dressing in a dry and then wet state. A dressing according to Example 1 was placed adhesive side up, dry, on top of the grey scale. Lines of demarcation numbering 0 to 19 between the shades of grey in the scale were then counted. A higher count indicates a greater transparency as more lines can be seen. When the dressing of Example 1 is dry, 7 lines of demarcation were seen. After wetting with water, 10 lines of demarcation could be seen for the dressing according to the invention. This result indicates that the dressing of Example 1 becomes more transparent on wetting.

The above demonstration was repeated using Tegaderm dressing which is made of an adhesive film and island of viscose absorbent material. With the dressing dry, 0 lines of demarcation could be seen. With the dressing wet 3 lines of demarcation could be seen. This result indicates that Tegaderm does not become transparent on absorption of exudate and is less transparent than the dressing of the invention.

The above demonstration was repeated using Mepore dressing ex Molnlyke. Like Tegaderm this is made of an adhesive film and island of viscose absorbent material. With the dressing dry, 0 lines of demarcation could be seen. With the dressing wet, 1 line of demarcation could be seen. This result shows that Mepore does not become transparent on absorption of exudate and is less transparent than the dressing of the invention.

Example 4

To measure the conformability of the dressing of Example 1, the force of elongation was measured. This is inversely proportional to the conformability. The force of elongation on the central dressing portion when wet and dry was measured and the results show an approximate 75% reduction in the force required to elongate the dressing to a 20% increase over its original length when wet.

The invention claimed is:

1. A wound dressing for post-operative sites comprising: a thin film layer of 0.02 mm to 0.04 mm in thickness covered on one side with an adhesive and an absorbent layer adhered to the adhesive side of the thin film layer, the absorbent layer being the wound contacting surface of the dressing, being made by carboxymethylating a cellulosic fabric, becoming transparent upon absorption of exudate, and allowing the wound to be viewed through the dressing on post-operative sites.

2. A wound dressing as claimed in claim 1 wherein the absorbent layer forms a gel on absorption of exudate.

3. A wound dressing as claimed in claim 2 wherein the absorbent layer is a carboxymethylated cellulose fabric with a degree of substitution of cellulose groups measured by IR spectroscopy in the range of from 0.12 to 0.35.

4. A wound dressing as claimed in claim 2 wherein the absorbent has an absorbency of at least 10 g/g of sodium/calcium chloride solution.

5. A wound dressing as claimed in claim 2 wherein the thin film layer is a polyurethane film.

6. A wound dressing as claimed in claim 2 wherein an apertured adhesive layer overlies the absorbent layer.

7. A wound dressing as claimed in claim 1 wherein the absorbent layer has a surface structure which provides a key for the adhesive of the thin film layer.

8. A wound dressing as claimed in claim 1 wherein the absorbent layer is a hydroentangled, non-woven fabric.

9. A wound dressing as claimed in claim 1 wherein the absorbent layer is a carboxymethylated cellulose fabric with a degree of substitution of cellulose groups measured by IR spectroscopy in the range of from 0.12 to 0.35.

10. A wound dressing as claimed in claim 1 wherein the absorbent layer has an absorbency of at least 10 g/g of sodium/calcium chloride solution.

11. A wound dressing as claimed in claim 1 wherein the thin film layer is a polyurethane film.

12. A wound dressing as claimed in claim 1 wherein the film layer extends beyond the absorbent layer to secure the dressing to the skin.

13. A wound dressing as claimed in claim 1 wherein an apertured adhesive layer overlies the absorbent layer.

14. A wound dressing as claimed in claim 1 wherein the thin film layer is transparent.

\* \* \* \* \*